(12) United States Patent
Tam

(10) Patent No.: US 8,133,369 B2
(45) Date of Patent: Mar. 13, 2012

(54) POTENTIOSTAT CIRCUIT

(75) Inventor: Simon Tam, Cambridge (GB)

(73) Assignee: Seiko Epson Corporation, Tokyo (JP)

( * ) Notice: Subject to any disclaimer, the term of this patent is extended or adjusted under 35 U.S.C. 154(b) by 1033 days.

(21) Appl. No.: 12/068,634

(22) Filed: Feb. 8, 2008

(65) Prior Publication Data

US 2008/0223719 A1 Sep. 18, 2008

(30) Foreign Application Priority Data

Feb. 9, 2007 (GB) .................................. 0702545.5

(51) Int. Cl.
*G01N 27/327* (2006.01)
*G01N 27/49* (2006.01)
*G01N 33/48* (2006.01)

(52) U.S. Cl. ................... 204/406; 204/400; 204/403.01; 204/412; 324/714

(58) Field of Classification Search .................. 204/406, 204/400, 403.01, 412; 324/691–724
See application file for complete search history.

(56) References Cited

U.S. PATENT DOCUMENTS

| | | | |
|---|---|---|---|
| 4,498,039 A | 2/1985 | Galwey et al. | |
| 5,198,771 A | 3/1993 | Fidler et al. | |
| 6,428,684 B1 * | 8/2002 | Warburton | 205/775 |
| 7,090,764 B2 * | 8/2006 | Iyengar et al. | 205/775 |
| 2004/0063152 A1 * | 4/2004 | Gumbrecht et al. | 435/7.1 |
| 2005/0247559 A1 | 11/2005 | Frey et al. | |

FOREIGN PATENT DOCUMENTS

JP A 2000-206088 7/2000

* cited by examiner

*Primary Examiner* — Jeffrey T Barton
*Assistant Examiner* — Jennifer Dieterle
(74) *Attorney, Agent, or Firm* — Oliff & Berridge, PLC (57) ABSTRACT

A potentiostat is provided for a biosensor circuit and permits sequential and simultaneous measurements to be performed at different cells across a matrix of biosensing devices. Accordingly, a potentiostat comprises a first differential amplifier for receiving a scanning voltage at a first input terminal and a voltage at the reference electrode at a second input terminal and for generating an output voltage at an output terminal to be applied to the working electrode, wherein, when in use, a feedback loop of the potentiostat circuit is closed between the reference electrode and the working electrode.

9 Claims, 8 Drawing Sheets

FIGURE 1a PRIOR-ART

FIGURE 1b PRIOR-ART

FIGURE 1c PRIOR-ART

Figure 3

Figure 2
PRIOR-ART

Figure 4  PRIOR-ART

POTENTIOSTAT CIRCUIT

BACKGROUND OF THE INVENTION

Several aspects of the present invention relate, in general, to a potentiostat and a biosensor circuit employing the potentiostat. The invention provides a multi-channel biosensor circuit having a potentiostat that enables sequential and simultaneous measurements to be performed at different cells across an array of biosensing devices.

1. Field of the Invention

A potentiostat is a measurement apparatus commonly used in the electrochemical field for executing voltammetric techniques. Cyclic voltammetry is a particularly useful voltammetric technique and aids the study of reversible reduction-oxidation (redox) reactions. When such techniques are applied to the biosensing field, a reversible redox reaction can take place at the interface between the surface of a biosensor selective receptive membrane (a bioreceptor) and an electrolyte.

2. Description of the Related Art

Figure 1A:
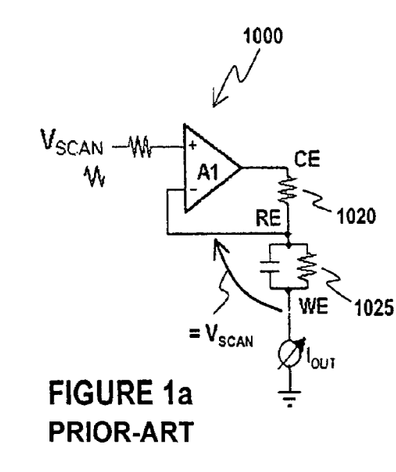
FIGS. 1a, 1b and 1c are schematic circuit diagrams of known potentiostats.
Figure 1B:
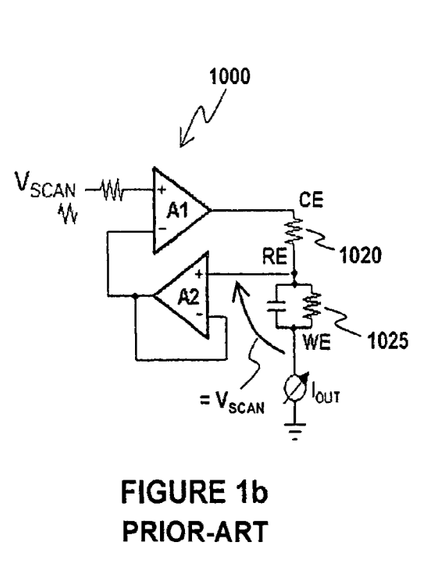
Figure 1C:
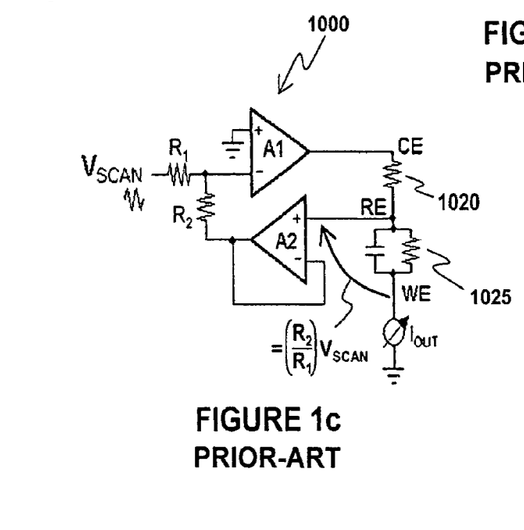
Figure 2:
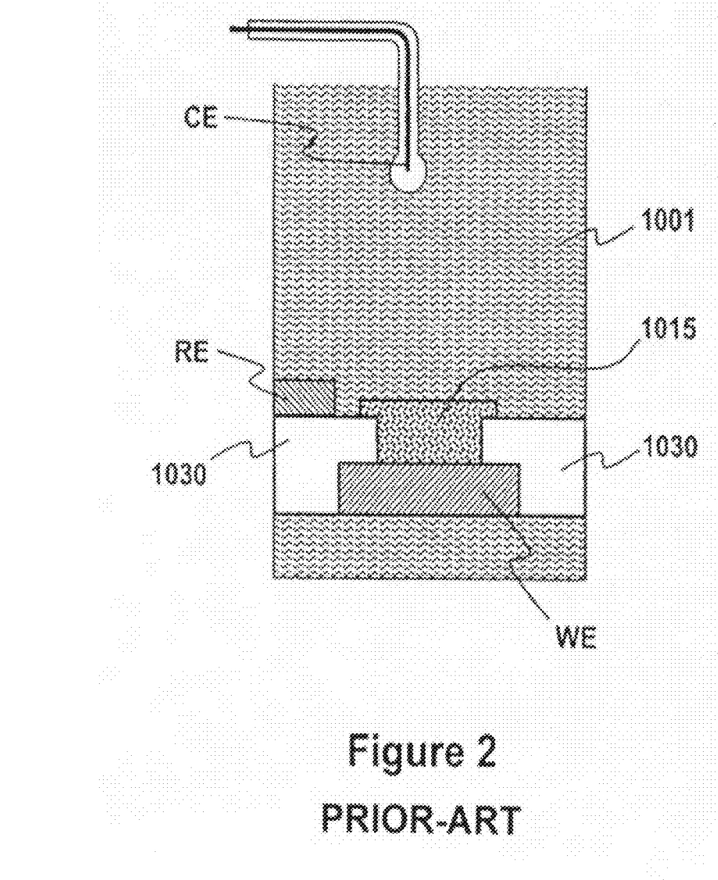
FIG. 2 is a schematic cross-sectional diagram of an electrochemical cell showing an interface between a sample solution and a bioreceptive layer undergoing cyclic voltammetric measurement.

Three examples of known potentiostat circuits are illustrated in FIGS. 1a to 1c. FIG. 2 is a cross-sectional schematic diagram of a sample undergoing cyclic voltammetric measurement using a potentiostat circuit of FIG. 1. Referring to FIG. 1, a potentiostat circuit 1000 is connected to a counter electrode CE, a reference electrode RE and a working electrode WE. As best shown in FIG. 2, the circuit is completed by a buffer solution containing samples under test, hereunder referred to as an analyte or electrolyte 1001, which is represented by a resistor 1020 in FIGS. 1a to 1c and a bioreceptor layer 1015, which is represented as a capacitor and resistor 1025 connected in parallel in FIGS. 1a to 1c. The reference electrode is separated from the working electrode WE by an insulating layer 1030 of, for example, $Si_3N_4$ in FIG. 2. The reference electrode RE draws no current and is positioned in close proximity to the working electrode WE in order to measure the voltage at the surface of the bioreceptor layer 1015 and close the feedback loop for a first operational amplifier A1. Once the feedback loop is closed, the high gain at the first operational amplifier A1 ensures that the voltage at the reference electrode, and hence the voltage at the surface of the bioreceptor layer 1015, with respect to the voltage at the working electrode equals $V_{SCAN}$, as shown in FIGS. 1a and 1b, or $—(R_2/R_1) V_{SCAN}$, as shown in FIG. 1c.

The bioreceptor layer 1015 may be a phage or enzyme that binds with a predetermined DNA or RNA strand, a peptide or another biological molecule, thereby changing the resistance and/or the capacitance of the circuit in which the electrodes are connected. Commonly the bioreceptor layer 1015 is known as a probe and the selective biological molecule it interacts with as a target. The characteristics of the capacitance and resistance as functions of applied voltage across them (in this case $V_{SCAN}$) vary if the target biological molecule bonds or reacts with the phage or the enzyme provided as the bioreceptor layer 1015, allowing the presence of the biological molecule to be detected. Specifically, the potentiostat circuit measures the current at the working electrode WE while a time varying voltage (reflected as the voltage at the reference electrode RE) and equal to $V_{SCAN}$ in the examples as shown in FIGS. 1a and 1b is applied at the surface of the bioreceptor layer.

Figure 3:
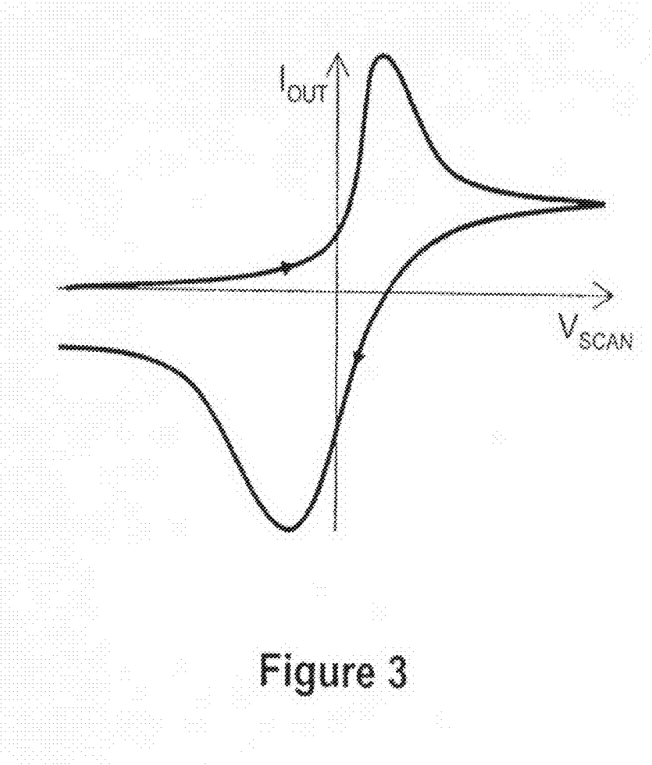
FIG. 3 is a schematic diagram of a theoretical measurement result of a sample undergoing cyclic voltammetric measurement.

A time varying periodic voltage signal is typically used as $V_{SCAN}$ in FIGS. 1a to 1c. This is beneficial when the potentiostat circuit is being used to measure a redox reaction, since the use of a DC voltage may affect the reaction. As $V_{SCAN}$ oscillates, the first half cycle promotes a reduction/oxidation reaction at the interface and the second half cycle promotes an oxidation/reduction reaction at the interface. As $V_{SCAN}$ varies, the rate of the reduction/oxidation reaction varies. At some points the reduction and oxidation reaction rates are at their maximum due to a diffusion of charge carrying species occurring due to the concentration gradient. The required charge transfer is supplied/removed at the working electrode. In operation, the reduction and oxidation reaction cycles are observed as a time varying current flow, $I_{OUT}(t)$ measured at the working electrode WE versus a cycle of scanning voltage, $V_{SCAN}(t)$. The voltage at the working electrode can be held at any DC reference level. The output of the circuit is typically a hysteresis loop with peaks pointing in opposite directions, as shown in FIG. 3. The shape of the hysteresis loop indicates whether a particular redox reaction has taken place, whether it is reversible and enables a user to study the rate of reaction by adjusting the scan rate dependency. The locations and magnitudes of the peaks are results of the reactants in equilibrium during the charge transfer that occurs in a redox reaction, and hence can be employed to extract the concentration of species in the analyte.

Figure 4:
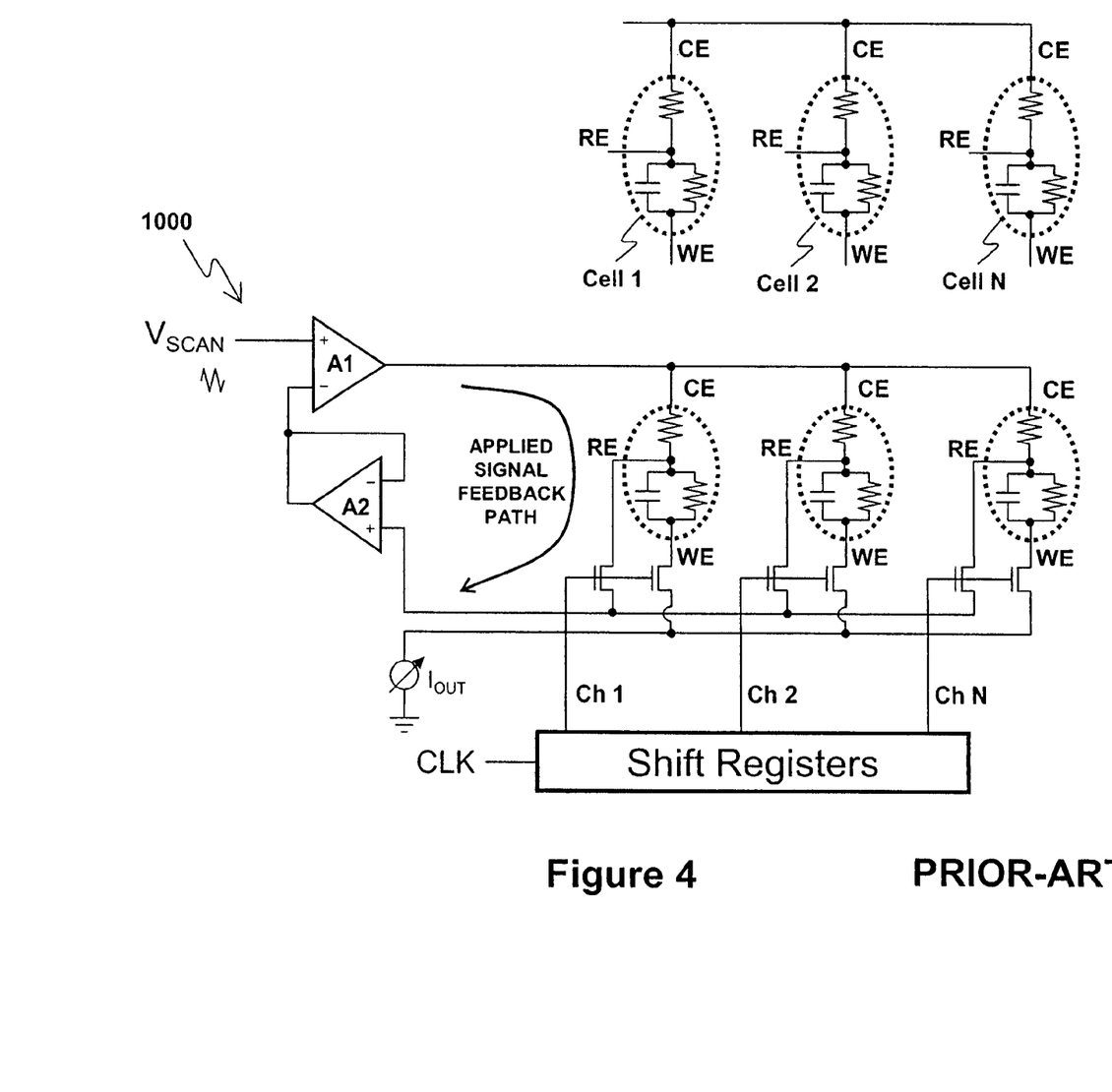
FIG. 4 is a schematic circuit diagram of a known multi-channel potentiostat.

A multi-channel potentiostat circuit is required for the analysis of a matrix of samples or to perform analysis a sample using a, matrix of bioreceptors. A known multi-channel potentiostat circuit is illustrated in FIG. 4. Referring to FIG. 4, a number of different matrix elements cell 1, cell 2, cell N, each share a common analyte or electrolyte. With such an arrangement, the counter electrodes CE of each matrix element cell 1, cell 2, . . . , cell N are connected together, meaning that effectively a single counter electrode CE is used. Each matrix element comprises a reference electrode RE disposed close to the surface of a bioreceptor layer (not shown in FIG. 4) and a working electrode WE with specific properties such as current sensitivity and dynamic range for the bioreceptor layer. Since each matrix element shares the same feedback loop between the counter electrode and each reference electrode, only one matrix element at a time may be used if the reference electrode is to be held at a required cyclic voltage $V_{SCAN}$. The matrix elements must therefore be selected and measured sequentially.

The cyclic voltage $V_{SCAN}$ that is applied to a cell typically requires measurement time of seconds to hundreds of seconds per cell. In the case of a DNA chip, the number of cells can increase to well over a thousand resulting in an integration time of hours as each cell is sequentially measured and read out. Also, in order to obtain a repeatable output, the number of cycles is large, which further increases measurement time. Furthermore, some samples may degrade or disintegrate during such long measurement periods, and expensive measures are required to keep them in a stable condition.

SUMMARY OF THE INVENTION

According to a first aspect of the present invention, there is provided a potentiostat comprising a first differential amplifier for receiving a scanning voltage at a first input terminal and a voltage of a reference electrode at a second input terminal and for generating an output voltage at an output terminal to be reflected at a working electrode, wherein, when in use, a feedback loop of the potentiostat circuit is closed between the reference electrode and the working electrode.

Preferably, the output voltage of the first differential amplifier is applied to a first input terminal of a first operational amplifier having a negative feedback between an output terminal and a second input terminal, wherein the working electrode is connected to the second input terminal of the first operational amplifier and held at the voltage of the first input terminal of the first operational amplifier.

More preferably, the first input terminal is a non-inverting input terminal and the second input terminal is an inverting input terminal.

The potentiostat may further comprise a second differential amplifier having a first input terminal connected to the output terminal of the first operational amplifier; and a second input terminal connected to the first input terminal of the first operational amplifier.

In that case, the first input terminal of the second differential amplifier may be an inverting input terminal and the second input terminal of the second differential amplifier may be a non-inverting input terminal.

The potentiostat may further comprise: a second operational amplifier having a first input terminal connected to the reference electrode; and an output terminal connected to the second input terminal of the first differential amplifier.

In another aspect, the present invention provides a single-channel biosensor circuit comprising: a counter electrode, a reference electrode, a working electrode, and a potentiostat circuit as described above.

In yet another aspect, the present invention provides a multi-channel biosensor circuit including a potentiostat as described above and further comprising: an array of counter electrodes, reference electrodes and working electrodes, each reference electrode in the array of reference electrodes being connected to a respective first terminal of a first switch; and each working electrode in the array of working electrodes being connected to a respective first terminal of a second switch, the first switch and the second switch each having a second terminal being connected to the potentiostat circuit, wherein outputs of a shift register unit are connected to a gate terminal of each respective first switch and each respective second switch and thereby adapted to select a counter electrode, reference electrode and working electrode in the array of for sequential readout by the potentiostat circuit.

The biosensor circuits may be capable of being read out simultaneously. Preferably, an input line is shared by each respective first differential amplifier of each respective potentiostat for receiving the scanning voltage. Alternatively, each first differential amplifier of each respective potentiostat may be connected to a respective input line for receiving the scanning voltage.

BRIEF DESCRIPTION OF THE DRAWINGS

Embodiments of the present invention will now be described, by way of example only, and with reference to the accompanying drawings in which.

Throughout the following description, like reference numerals shall be used to identify like parts.

DESCRIPTION OF THE PREFERRED EMBODIMENTS

Figure 5A:
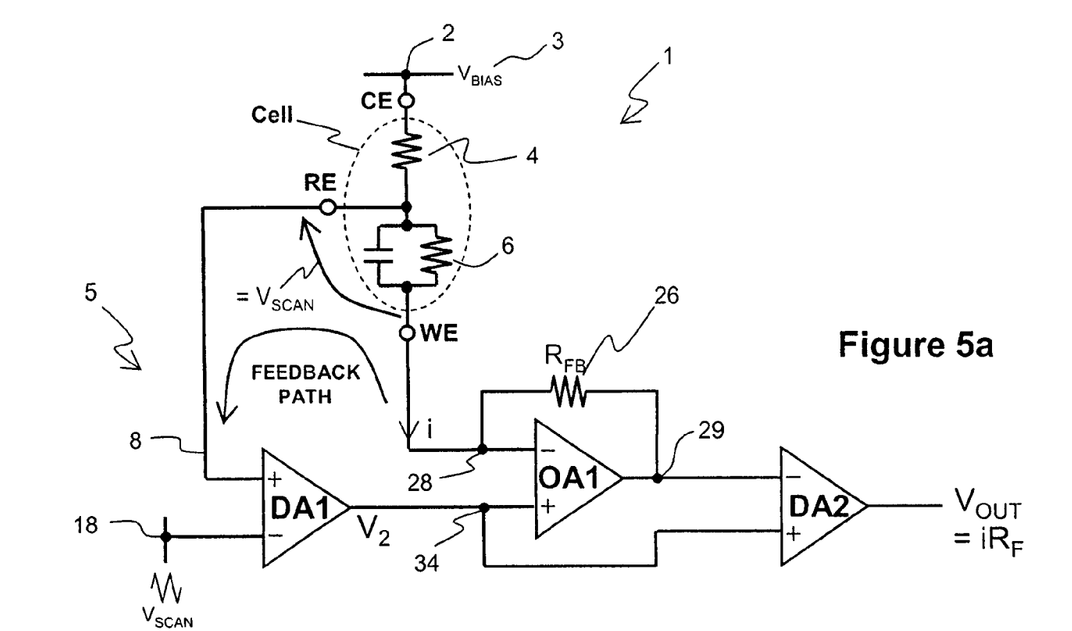
FIG. 5a is a schematic circuit diagram of a biosensor including a potentiostat suitable for use in a multi-channel biosensor according to a first embodiment of the present invention.

Referring to FIG. 5a, a first embodiment of the present invention comprises a biosensor circuit 1 consisting of a three terminal electrochemical cell, differential amplifiers and a current-to-voltage converter, with a feedback voltage signal path formed between the working electrode WE and the reference electrode RE. The three terminal electrochemical cell is formed using the counter electrode CE, the reference electrode RE and the working electrode WE. The counter electrode CE is connected to a first voltage supply rail 2 connected to a bias voltage $V_{BIAS}$ 3. A first resistor 4 is connected between the counter electrode CE and a reference electrode RE and represents an electrolyte comprising at least one target biological molecule. In a similar manner to that illustrated in FIG. 2, the reference electrode RE is disposed upon an insulator (not shown in FIG. 5) in close proximity to a working electrode WE, which is disposed upon a bioreceptive layer modeled in FIG. 5a by a parallel resistor and capacitor arrangement 6.

The reference electrode RE is connected to a potentiostat circuit 5. The reference electrode RE, which draws very little or zero current, is connected to a non-inverting input terminal 8 of a first differential amplifier (or difference amplifier) DA1 with a gain of unity. The inverting input terminal of the first differential amplifier DA1 is connected to a second voltage supply rail 18 for providing a cyclic voltage $V_{SCAN}$. The output terminal 34 of the first differential amplifier DA1 is connected to a non-inverting input terminal of a first operational amplifier OA1 configured as a current-voltage converter.

The inverting input of the first operational amplifier OA1 is connected to the working electrode WE. The output terminal of the first operational amplifier OA1 is connected to a first terminal of a second resistor 26 configured as a feedback resistor in the current-voltage converter. The second terminal of the second resistor 26 is connected to a fourth node 28 located between the working electrode WE and the inverting input of the first operational amplifier OA1.

The output terminal of the first operational amplifier OA1 is also connected to an inverting input terminal of a second differential amplifier DA2. The non-inverting input terminal of the second differential amplifier DA2 is connected to the output terminal 34 of the first differential amplifier DA1 and a non-inverting input terminal of the first operational amplifier OA1. An output terminal of the second differential amplifier is connected to an output stage (not shown in FIG. 5).

Figure 5B:
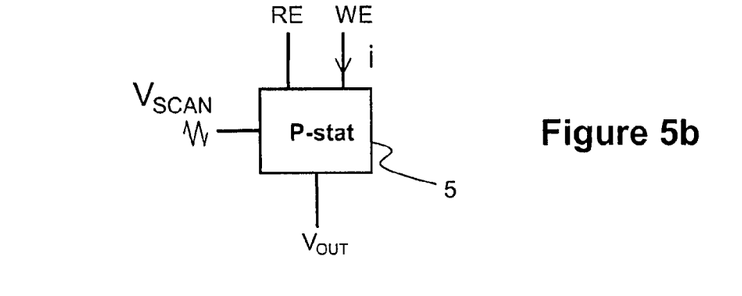
FIG. 5b is a schematic block diagram of a potentiostat suitable for use in a multi-channel biosensor according to the first embodiment of the present invention.

Referring to FIG. 5b, the potentiostat circuit 5 is represented as a schematic block diagram having inputs: $V_{SCAN}$, the voltage of the reference electrode RE and the current i drawn by the working electrode WE. The potentiostat also comprises an output terminal in order to generate an output voltage, $V_{OUT}$.

Figure 6:
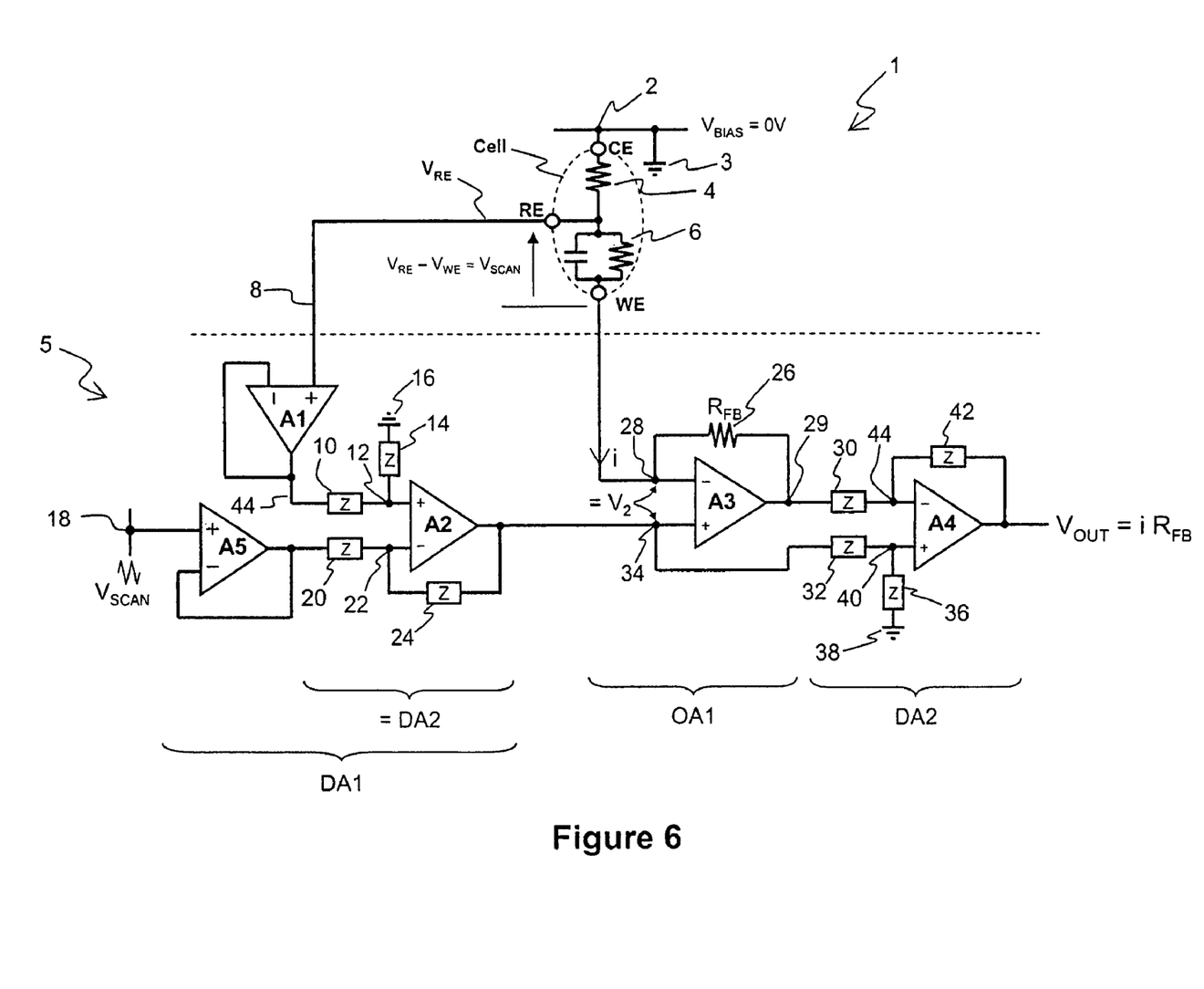
FIG. 6 is a schematic circuit diagram of a biosensor including a potentiostat suitable for use in a multi-channel biosensor according to a second embodiment of the present invention.

Referring to FIG. 6, a second embodiment of the present invention comprises of a biosensor circuit 1, consisting of a three terminal electrochemical cell, differential amplifiers and a current-to-voltage converter, with a feedback voltage signal path formed between the working electrode WE and the reference electrode RE. The three terminal electrochemical cell is formed using the counter electrode CE, the reference electrode RE and the working electrode WE. The counter electrode CE is connected to the first voltage supply rail 2 connected to a bias voltage $V_{BIAS}$ 3 equal to the system ground. A first resistor 4 is connected between the counter electrode CE and a reference electrode RE and represents an electrolyte comprising at least one target biological molecule. In a similar manner to that illustrated in FIG. 2, the reference electrode RE is disposed upon an insulator (not shown in FIG. 6) in close proximity to a working electrode WE, which is disposed upon a bioreceptive layer represented in FIG. 6 by a parallel resistor and capacitor arrangement 6.

The reference electrode RE and working electrode WE are connected to a potentiostat circuit 5. The reference electrode RE is connected to the non-inverting input of the differential amplifier DA1 comprising operational amplifiers A1, A2 and A5, and first, second, third and fourth impedance loads. The non-inverting input of the first differential amplifier DA1 is formed by the non-inverting input of an operational amplifier A1 with a high open-loop gain. The operational amplifier A1 is configured to operate as a unity gain voltage follower by connecting its inverting input to its output terminal. It is preferable to provide an operational amplifier A5, identical to the operational amplifier A1, with the output of the operational connected to the inverting input to compensate the input offset voltage of the operational amplifier A1. The non-inverting input of the operational amplifier A5 forms the inverting input of the first differential amplifier DA1 and is connected to a supply rail node 18 that provides a cyclic voltage $V_{SCAN}$. The non-inverting input 12 of the operational amplifier A2 is connected to the first terminal of the first impedance load 10 and the first terminal of the second impedance load 14. The second terminal of the first impedance load is connected to the output terminal of the operational amplifier A1. The second terminal of the second impedance load is connected to the system ground 16. The inverting input 22 of the operational amplifier A2 is connected to the first terminal of the third impedance load 20 and the first terminal of the fourth impedance load 24. The second terminal of the third impedance load 20 is connected to the output terminal of the operational amplifier A5, effectively connected to the scanning voltage $V_{SCAN}$ at node 18. The second terminal of the fourth impedance load is connected to the output terminal of the operational amplifier A2. It is preferable to provide the same values for the first to the fourth impedance loads and obtain a voltage $V_2$ equals $V_{RE}-V_{SCAN}$ at node 34.

The inverting input 28 of the operational amplifier A3 with a very high open-loop gain is connected to the working electrode WE. A feedback resistor $R_{FB}$ 26 is connected between the inverting input 28 and the output terminal 29 of the operational amplifier A3, forming a current-to-voltage converter. The high open-loop gain of A3 forces the voltages at the inverting and non-inverting inputs to be equal. As a result, the local voltage difference between the reference electrode RE and working electrode WE, $V_{RE}-V_{WE-VSCAN}$, induces a current i caused by the redox reaction at the bioreceptor interface. This current i flows from the working electrode 28, through the feedback resistor $R_{FB}$ 26 to node 29 and generate a voltage at node 29 equals $V_{WE}$-i $R_{FB}$.

The second differential amplifier DA2 comprises an operational amplifier A4 with its non-inverting input 40 connected to the first terminal of the fifth impedance load 32 and the first terminal of the sixth impedance load 36. The second terminal of the fifth impedance load 32 is connected to node 34 that forms the non-inverting input of the operational amplifier OA1. The second terminal of the sixth impedance load 36 is connected to the system ground 38. The inverting input 44 of the operational amplifier A4 is connected to the first terminal of the seventh impedance load 30 and the first terminal of the eighth impedance load 42. The second terminal of the seventh impedance load 30 is connected to node 29 that forms the output of the operational amplifier OA1. The second terminal of the eighth impedance load 42 connects to the output of the operational amplifier A4. It is preferable to provide all impedance loads equal in value and obtain an output voltage at the operational amplifier A4 equal to i $R_{FB}$.

The implementation of DA1 and DA2 are not limited to the example embodiment shown in FIG. 6. Both differential amplifiers DA1 and DA2 are required to provide an output equal to the difference of their inputs with unity gain. The differential amplifier DA1 is required to draw minimal current from the reference electrode RE and the differential amplifier DA2 is required to provide sufficient output current for the subsequent stage. To simplify the design, DA1 consists of DA2 with additional operational amplifiers A1 and A5 configured as voltage followers at both inverting and non-inverting inputs to minimise the input current. Operational amplifier A5 is optional, but its presence is preferable because a matched pair of A1 and A5 will allow the cancellation of their inherited offset voltages and hence minimize the output error at operational amplifier A2 configured as differential amplifiers.

Figure 7:
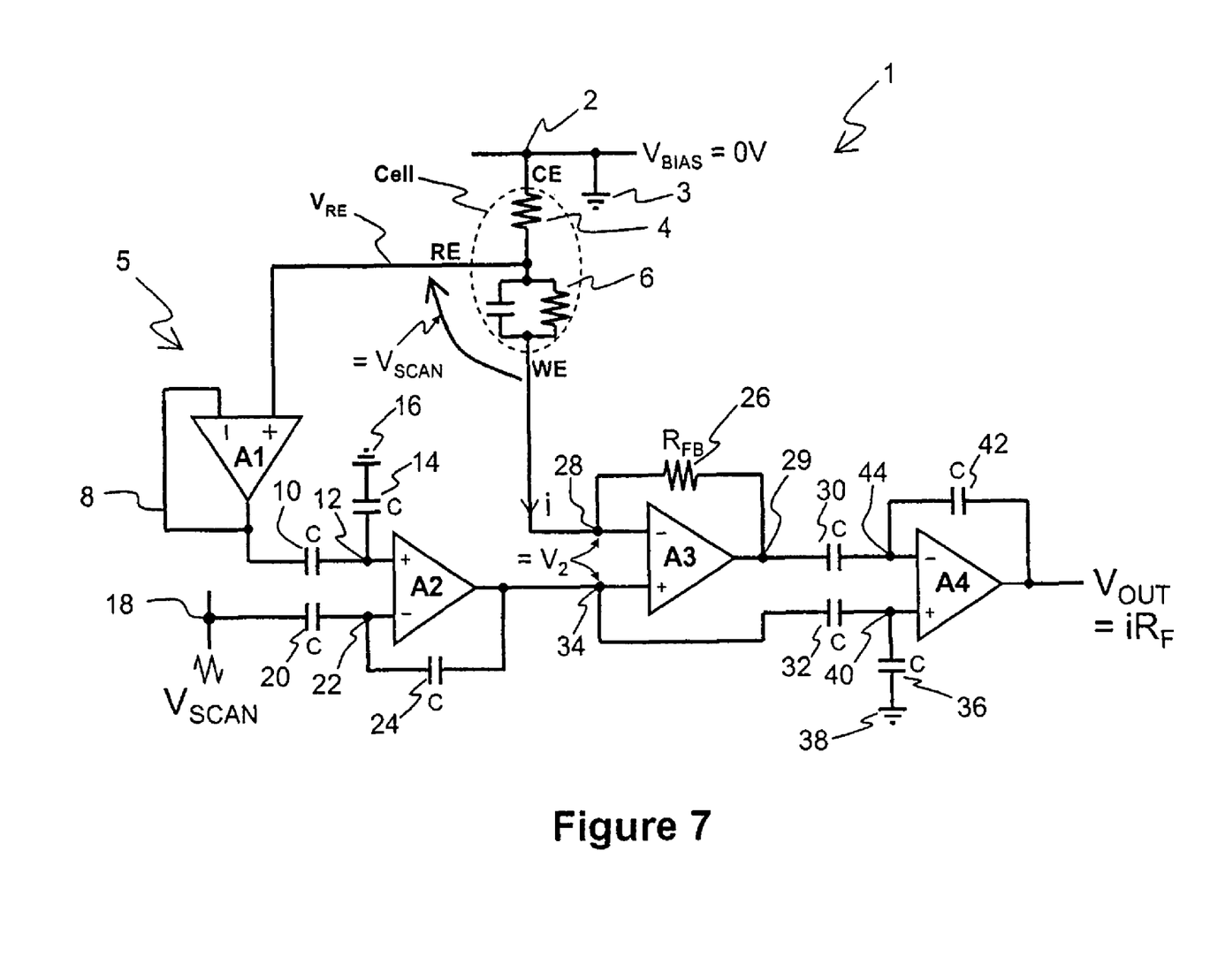
FIG. 7 is a schematic circuit diagram of a biosensor including a potentiostat suitable for use in a multi-channel biosensor according to a third embodiment of the present invention.

Referring to FIG. 7, a third embodiment of the present invention is the same as the second embodiment, except that all impedance loads are implemented with capacitive loads. It is preferable to have all capacitive loads equal to C.

Figure 8A:
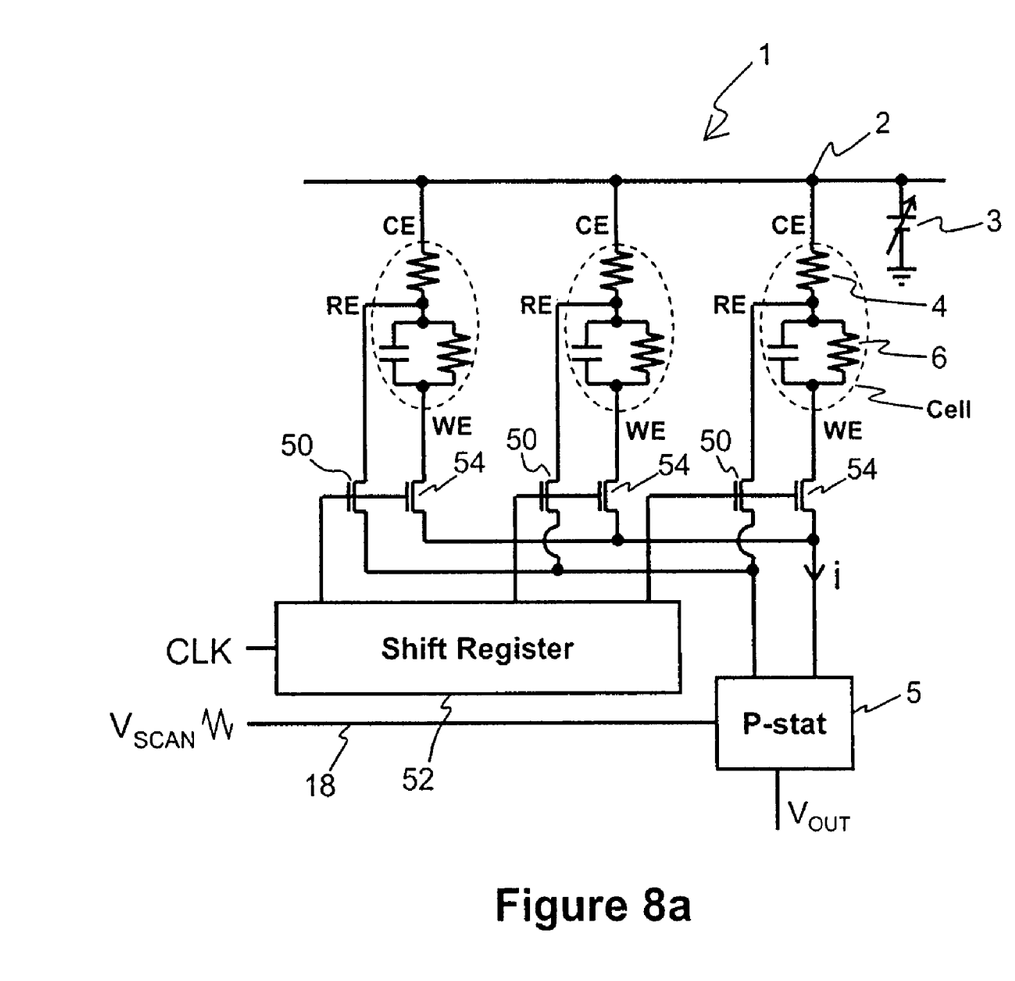
FIG. 8a is a schematic circuit diagram of a multi-channel biosensor employed for sequential readout according to a fourth embodiment of the present invention.

Referring to FIG. 8a, a multi-channel biosensor circuit 1 is arranged for sequential readout according to an embodiment of the present invention and comprises an array of counter electrodes CE, reference electrodes RE, working electrodes WE, electrolytes and bioreceptor layers.

The counter electrodes CE are connected to a first voltage supply rail 2 connected to ground or a DC voltage source 3. Each counter electrode CE is connected to a first terminal of a first resistor 4 having a second terminal connected to the reference electrode RE. The first resistor 4 represents the electrolyte comprising at least one target biological molecule. In a similar manner to that illustrated in FIG. 3, the reference electrode RE is disposed upon an insulator (not shown in FIG. 8a) in close proximity to a working electrode WE, which is disposed adjacent a bioreceptor layer represented in FIG. 8a by a parallel resistor and capacitor arrangement 6.

Each reference electrode RE is connected to a first terminal of a respective first transistor 50 having a gate terminal connected to a shift register 52 and a second terminal connected a first input terminal of a potentiostat circuit 5. Each working electrode WE is connected to a first terminal of a respective second transistor 54 having a gate terminal connected to the shift register 52 and a third terminal connected to a second input terminal of the potentiostat circuit 5. The potentiostat circuit 5 has a third input terminal connected to a second voltage supply rail 18 to receive a voltage $V_{SCAN}$, which is also applied to an input terminal of the shift register 52. The potentiostat circuit 5 comprises an output terminal for outputting a generated voltage $V_{OUT}$.

Figure 8B:
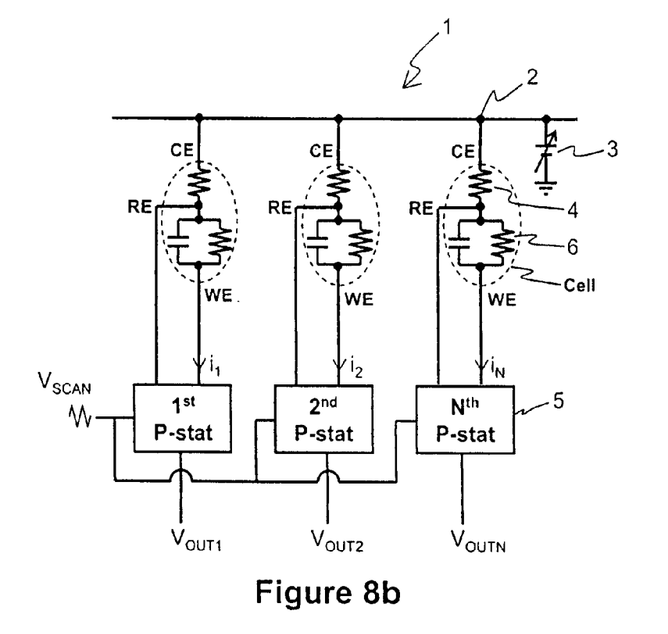
FIG. 8b is a schematic circuit diagram of a multi-channel biosensor employed for simultaneous readout according to a fifth embodiment of the present invention.

Referring to FIG. 8b, a multi-channel biosensor circuit 1 is arranged for simultaneous readout according to a third embodiment of the present invention and comprises an array of counter electrodes CE, reference electrodes RE, working electrodes WE, electrolytes, bioreceptor layers and potentiostat circuits 5.

The counter electrodes CE are connected to a first voltage supply rail 2 connected to ground or a DC voltage source 3. Each counter electrode CE is connected to a first terminal of a first resistor 4 having a second terminal connected to the reference electrode RE. The first resistor 4 represents the electrolyte comprising at least one target biological molecule. In a similar manner to that illustrated in FIG. 3, the reference electrode RE is disposed upon an insulator 30 (not shown in FIG. 8b) in close proximity to a working electrode WE, which is disposed adjacent a bioreceptor layer represented in FIG. 8b by a parallel resistor and capacitor arrangement 6.

Each reference electrode RE is connected to a first input terminal of a respective Nth potentiostat circuit 5 and each working electrode is connected to a second input terminal of the respective $N^{th}$ potentiostat circuit 5. Each Nth potentiostat circuit 5 comprises a third input terminal to receive a voltage $V_{SCAN}$ and an output terminal for outputting a generated voltage $V_{OUT}$.

In operation of the multi-channel biosensor circuit 1 according to this embodiment of the present invention, the counter electrode CE is held at a fixed, ground potential. The circuit is completed by an analyte or electrolyte represented by the resistor 4, and a bioreceptor layer represented as the parallel resistor and capacitor arrangement 6. As current flows through the electrochemical cell, the reference electrode RE is self-adjusted to a voltage $V_{RE}$. Without drawing any current, this voltage is detected by the non-inverting input terminal of the first amplifier A1 which is configured as a voltage follower, and copied to its output terminal in order to avoid upsetting the operation of the electrochemical cell. The output voltage is then applied to the non-inverting input terminal of the second amplifier A2 (in FIGS. 6 and 7).

A cyclic scanning voltage $V_{SCAN}$ is applied to the inverting input terminal of the second amplifier A2. The second amplifier A2 and its corresponding impedance loads 10, 14, 20 and 24, form a differential amplifier with unity gain, giving an output voltage $V_2=(V_{RE}-V_{SCAN})$, which is applied to the non-inverting input terminal of the third amplifier A3.

The voltage of the working electrode WE is controlled and adjusted by the output voltage $V_2$ of the second amplifier A2 by applying the Virtual Earth Theory to the third amplifier A3. Due to a high open-loop gain in the third amplifier A3, and the use of a second resistor 26 for negative feedback, the voltages at the inverting and non-inverting inputs of the third amplifier A3 are effectively equal. Therefore, the voltage of the working electrode WE equal to $V_2=(V_{RE}-V_{SCAN})$. The current drawn at the working electrode WE is converted to an output voltage $=(V_2 - i R_{FB})$ by the third amplifier A3 configured as a current-voltage converter. This output voltage is applied to the inverting input 29 of the differential amplifier formed by the fourth amplifier A4 and corresponding impedance loads 30, 32, 42 and 36. The non-inverting input of this differential amplifier, node 34, is connected to the output of the second amplifier A2. As a result, the output voltage $V_{OUT}$, given by $V_{OUT}=i R_{FB}$ is generated.

Of course, it will be understood that the embodiment illustrated in FIG. 5 operates in a corresponding manner.

In operation of the multi-channel biosensor of FIG. 8a employed for sequential readout in the present invention, the circuit of FIG. 8a is characterised by the presence of the shift register 52, the plurality of switching transistors 50, 54 and also the potentiostat circuit 5. The counter electrode CE can be at a fixed ground potential or at an arbitrary DC voltage. The potentiostat circuit 5 described above with reference to FIGS. 5 to 7 is represented by a block diagram having inputs $V_{SCAN}$, the voltage of the reference electrode $V_{RE}$ and the current i drawn by the working electrode WE in order to generate an output voltage, $V_{OUT}$.

In order to sequentially readout an individual cell, the reference electrode RE and the working electrode WE of the individual cell are selected by the shift register 52 by applying a signal to the gate terminal of the respective first and second transistors 50, 54. A voltage the same as the voltage of the reference electrode $V_{RE}$ is established at the surface of the bioreceptor layer and the voltage of the working electrode $V_{WE}$ can be controlled such that $V_{RE}-V_{WE}=V_{SCAN}$ through the virtual earth of the operational amplifier (OA1 or A3) responsible for current-to-voltage conversion, as discussed above in connection with the description of FIGS. 5 to 7. Successive individual cells can be sequentially selected by the shift register 50.

In operation of the multi-channel biosensor of FIG. 8b employed for simultaneous readout in the present invention, the circuit of FIG. 8b is characterised by the presence of N-number of potentiostat circuits 5. The common counter electrodes 2 are held at a fixed ground potential or at an arbitrary DC voltage 3. Since each potentiostat circuit 5 comprises an individual, closed feedback loop, the output voltage $V_{OUT}$ can be read out for each cell simultaneously. The arrangement enables the dropping of a biosensor circuit 1 within a testing vessel comprising an analyte and subsequently the reading out of the generated output voltages $V_{OUT}$ for each of the potentiostat circuits simultaneously. Chemical crosstalk of reaction materials between adjacent cells can be prevented by providing sufficient physical spacing.

The foregoing description has been given by way of example only and it will be appreciated by a person skilled in the art that modifications can be made without departing from the scope of the present invention.

Figure 8C:
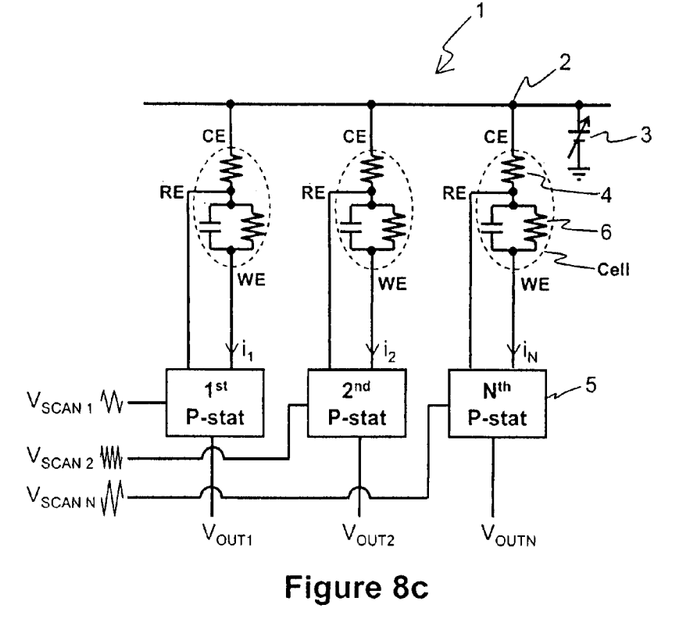
FIG. 8c is a schematic circuit diagram of a multi-channel biosensor employed for simultaneous readout according to a sixth embodiment of the present invention.

The voltage $V_{SCAN}$ applied to each potentiostat 5 illustrated in FIG. 8b can be applied separately to each potentiostat 5 thereby enabling a different value of $V_{SCAN}$ to be applied to each potentiostat 5, as shown in FIG. 8c.

In addition, FIG. 5 is a simplified schematic of the potentiostat circuit 5 and reset switches may be used where appropriate. One counter electrode can be employed for the potentiostat circuits 5 illustrated in FIGS. 8a to 8c. The biosensor circuit 1 of FIGS. 8a to 8c can be located on a single chip or substrate and since the cell area is large, space remains to incorporate additional circuits to include auto-zero amplifiers, peak detection and discrimination and digitisation means.

The shape of the input voltage $V_{SCAN}$ is not limited to a triangular waveform. It can be of sawtooth waveform, sinusoidal waveform, square waveform, or pulses including varying mark-space ratios. The input voltage $V_{SCAN}$ is not limited to a cyclic AC voltage. $V_{SCAN}$ can be a constant voltage applied to a DC differential amplifier in place of the second amplifier A2. In this embodiment, the first capacitor 10, the second capacitor 14, the third capacitor 20 and the fourth capacitor 24 are replaced by resistors or other impedance loads as is known in the art. A DC differential amplifier can also be used in place of the fourth amplifier A4.

The invention claimed is:

1. A biosensor circuit comprising a counter electrode, a reference electrode, a working electrode and a potentiostat circuit, the potentiostat circuit, comprising:
   a first differential amplifier that receives a scanning voltage at a first input terminal and the voltage of the reference electrode at a second input terminal, and generate an output voltage at an output terminal applied to the working electrode, a feedback loop of the potentiostat circuit being closed between the reference electrode and the working electrode;
   a first operational amplifier;
   the output voltage of the first differential amplifier being applied to a first input terminal of the first operational amplifier, which has a negative feedback between an output terminal and a second input terminal, and the working electrode being connected to the second input terminal of the first operational amplifier and held at the voltage of the first input terminal of the first operational amplifier; and
   a second differential amplifier having a first input terminal connected to the output terminal of the first operational amplifier and a second input terminal connected to the first input terminal of the first operational amplifier.

2. The biosensor circuit according to claim 1, the first input terminal of the first operational amplifier being a non-inverting input terminal and the second input terminal of the first operational amplifier being an inverting input terminal.

3. The biosensor circuit according to claim 1,
   the first input terminal of the second differential amplifier being an inverting input terminal; and
   the second input terminal of the second differential amplifier being a non-inverting input terminal.

4. The biosensor circuit according to claim 1, further comprising:
   a second operational amplifier having a first input terminal connected to the reference electrode; and
   an output terminal connected to the second input terminal of the first differential amplifier.

5. The biosensor circuit according to claim 1, wherein the biosensor circuit is a single-channel biosensor circuit.

6. A multi-channel biosensor circuit including the biosensor circuit according to claim 1, further comprising:
   an array of counter electrodes, reference electrodes and working electrodes, each reference electrode in the array of reference electrodes being connected to a respective first terminal of a first switch; and
   each working electrode in the array of working electrodes being connected to a respective first terminal of a second switch,
   the first switch and the second switch each having a second terminal being connected to the potentiostat circuit, wherein
   outputs of a shift register unit are connected to a gate terminal of each respective first switch and each respective second switch and thereby adapted to select a counter electrode, reference electrode and working electrode in the array for sequential readout by the potentiostat circuit.

7. A multi-channel biosensor circuit, comprising:
   an array of the single-channel biosensor circuits according to claim 5, each biosensor circuit of the array of the single-channel biosensor circuits being configured to read out simultaneously.

8. The multi-channel biosensor circuit according to claim 7, an input line being shared by each respective first differential amplifier of each respective potentiostat circuit for receiving the scanning voltage.

9. The multi-channel biosensor circuit according to claim 7, each first differential amplifier of each respective potentiostat circuit being connected to a respective input line for receiving the scanning voltage.

* * * * *